US008460935B2

(12) United States Patent
Kurono et al.

(10) Patent No.: US 8,460,935 B2
(45) Date of Patent: Jun. 11, 2013

(54) SAMPLE ANALYZER, SAMPLE ANALYZING METHOD, AND COMPUTER PROGRAM PRODUCT

(75) Inventors: Hiroshi Kurono, Kobe (JP); Keitarou Kondou, Kobe (JP)

(73) Assignee: Sysmex Corporation, Hyogo (JP)

( * ) Notice: Subject to any disclaimer, the term of this patent is extended or adjusted under 35 U.S.C. 154(b) by 37 days.

(21) Appl. No.: 12/706,438

(22) Filed: Feb. 16, 2010

(65) Prior Publication Data

US 2010/0210019 A1 Aug. 19, 2010

(30) Foreign Application Priority Data

Feb. 17, 2009 (JP) ................. 2009-033722

(51) Int. Cl.
*G01N 35/00* (2006.01)
*G01N 33/86* (2006.01)
*G01N 31/00* (2006.01)

(52) U.S. Cl.
USPC ........ 436/8; 436/43; 436/50; 436/55; 436/63; 436/69; 436/180; 422/67; 422/73

(58) Field of Classification Search
USPC .................. 436/8, 43, 45, 47, 48, 50, 55, 63, 436/69, 180; 422/63, 64, 65, 67, 73
See application file for complete search history.

(56) References Cited

U.S. PATENT DOCUMENTS

| 2005/0123445 | A1* | 6/2005 | Blecka et al. ................... 422/64 |
| 2005/0175503 | A1* | 8/2005 | Shiba et al. ..................... 422/64 |
| 2008/0063570 | A1 | 3/2008 | Fujino et al. |
| 2008/0241939 | A1* | 10/2008 | Matsuo et al. .................. 436/54 |
| 2010/0104478 | A1* | 4/2010 | Kondou ........................ 422/100 |

FOREIGN PATENT DOCUMENTS

JP 2004-271265 A 9/2004

* cited by examiner

*Primary Examiner* — Maureen Wallenhorst
(74) *Attorney, Agent, or Firm* — Sughrue Mion, PLLC

(57) ABSTRACT

A sample analyzer is provided. The sample analyzer includes a reagent container holder, a measurement unit, and an information processing unit configured to perform operations including controlling the measurement unit to start the successive measurement of the plurality of samples, determining whether to switch from the first reagent container to the second reagent container while performing the successive measurement by using the reagent contained in the first reagent container, controlling the measurement unit to suspend a start of aspiration of a next sample, to measure a quality control measurement sample prepared from the reagent contained in the second reagent container, when determined to switch from the first reagent container to the second reagent container, and controlling the measurement unit to start the aspiration of the next sample when an analysis result of the quality control measurement sample meets a predetermined condition.

21 Claims, 10 Drawing Sheets

F I G. 3
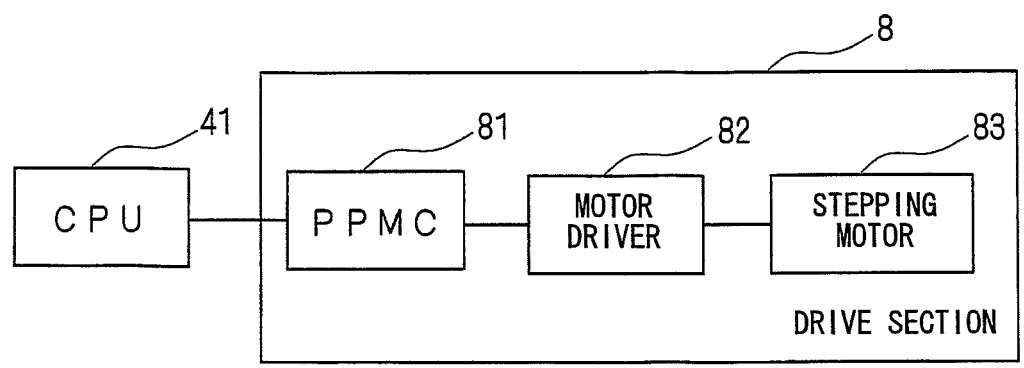

FIG. 9

ASSAY SETTING

MEASUREMENT ITEM — 901

PTTPC+
APTT ACTIN
Fibrinogen
TTO
HpT
Factor II
Factor V
Factor VII
Factor VIII
Factor IX
Factor X
Factor XI
Factor XII
BC Antithrombin III
BC α2-Antiplasmin
BC Plasminogen
BC Protein C
LPIA FDP
LPIA D-Dimer
U-FDP
PIC
PT THS
PT INN
TC PT
TC PT+
APTT FS
APTT FSL
APTT PSL
TC APTT
APTT-SLA
TC Fib
TC Fib-L
SIRC VIII
SIRC AT3
SIRC APL

| BASIC SETTING | REMEASUREMENT SETTING | REFLECT SETTING | QUALITY CONTROL SETTING | TEST PROTOCOL SETTING |

| CONTROL | PERIODICAL AUTOMATIC QC | TIME INTERVAL | VIAL QC | NUMBER OF TIMES OF MEASUREMENT | DILUTION RATE | ASSAY PARAMETER LIST |
|---|---|---|---|---|---|---|
| CtIN | OFF | | 0 OFF | 1 | 1/1 | PTsec |
| Citrol1 | OFF | | 0 OFF | 1 | 1/1 | PTsecPT% |

ADD  DELETE  ← →

QUALITY CONTROL SETTING
CONTROL: Citrol1

☑ PTsec
☑ PT%
☐ PTR
☐ PTINR

DETERMINATION RULE SETTING — 902

AUTOMATIC QC   ☑ USE FOR QUALITY CONTROL

☐ PERIODICAL AUTOMATIC QC    ☐ TIME
☐ VIAL QC

— 903

MEASUREMENT CONDITION
DILUTION RATE: 1/1  ▶
NUMBER OF TIMES OF MEASUREMENT: 1  ▶

CREATE COPY  ← →
DELETE

EXPORT   ADD   READ   PRINT   REGISTER   CLOSE

SAMPLE ANALYZER, SAMPLE ANALYZING METHOD, AND COMPUTER PROGRAM PRODUCT

FIELD OF THE INVENTION

The present invention relates to a sample analyzer for analyzing a measurement result of a measurement sample prepared from a sample and a reagent, a sample analyzing method, and a computer program product.

BACKGROUND

In an analyzer for analyzing a measurement result of a measurement sample prepared from a sample and a reagent, the sample is contained in a sample container and the reagent is contained in a reagent container. There are some reagents whose quality starts deteriorating immediately after the reagent containers are unsealed. Conventionally, in a case where a plurality of reagent containers each containing the same kind of reagent are set in the analyzer, at the time when the amount of the reagent contained in one reagent container has become less than a predetermined amount, quality control of the reagent remaining in another reagent container is conducted. In this manner, it is determined whether or not the reagent to be used has deteriorated.

For example, Japanese Patent Publication No. 2004-271265 discloses an automatic analyzer that performs, when the number of remaining tests performable with a reagent contained in one reagent container has become less than a preset number of tests, an analysis of a sample that is used for quality control (hereinafter referred to as a quality control sample) by using the reagent contained in another reagent container. When an analysis result of the quality control sample is determined to be abnormal, the reagent contained in the another reagent container is suspected to be deteriorated, and therefore, needs to be replaced.

However, in the automatic analyzer disclosed in Japanese Patent Publication No. 2004-271265, when the preset number of remaining tests is too small, analysis process by the automatic analyzer is not stopped until the analysis result of the quality control sample is obtained. Thus, the analysis process of samples using the reagent contained in the another reagent container is continued. Accordingly, when the analysis result of the quality control sample is determined to be abnormal, the samples which have been measured by using the reagent suspected to be deteriorated need to be measured again. Therefore, there is a problem that samples are consumed in vain.

Meanwhile, in a case where the preset number of remaining tests is too large, the quality control sample is analyzed when a sufficient amount of the reagent is remaining in the one reagent container. This allows that the analysis result of the quality control sample is obtained before samples are analyzed by using the reagent contained in the another reagent container. However, in a case where it takes long time until the analysis process of samples using the reagent contained in the another reagent container is performed after the analysis process of the quality control sample, the reagent in the another reagent container may deteriorate after the performance of the analysis process of the quality control sample. This makes it difficult to perform proper quality control of reagents.

SUMMARY

The scope of the present invention is defined solely by the appended claims, and is not affected to any degree by the statements within this summary.

A first aspect of the present invention is a sample analyzer comprising: a reagent container holder capable of holding a first reagent container and a second reagent container, each of which contains a same kind of reagent; a measurement unit for aspirating a sample to be measured, and for measuring a measurement sample prepared from the sample and the reagent contained in the first reagent container or the second reagent container; and an information processing unit configured to perform operations comprising: receiving a start instruction to start successive measurement of a plurality of samples; controlling the measurement unit so as to start the successive measurement of the plurality of samples according to the reception of the start instruction; determining whether or not to switch from the first reagent container to the second reagent container while the measurement unit is performing the successive measurement by using the reagent contained in the first reagent container; controlling the measurement unit so as to suspend a start of aspiration of a next sample, to aspirate a quality control sample, and to measure a quality control measurement sample prepared from the quality control sample and the reagent contained in the second reagent container, when determined to switch from the first reagent container to the second reagent container; and controlling the measurement unit so as to start the aspiration of the next sample when an analysis result of the quality control measurement sample meets a predetermined condition.

A second aspect of the present invention is a sample analyzer comprising: a reagent container holder capable of holding a first reagent container and a second reagent container, each of which contains a reagent of a same kind; a measurement unit for aspirating a sample to be measured, and for measuring a measurement sample prepared from the sample and the reagent contained in the first reagent container or the second reagent container; and an information processing unit configured, to perform operations comprising: receiving a start instruction to start successive measurement of a plurality of samples; controlling the measurement unit so as to aspirate one sample and to measure a measurement sample prepared from the one sample and the reagent contained in the first reagent container according to the reception of the start instruction; determining whether or not to switch from the first reagent container to the second reagent container after the aspiration of the one sample; controlling the measurement unit so as to suspend a start of aspiration of a next sample, to aspirate a quality control sample, and to measure a quality control measurement sample prepared from the quality control sample and the reagent contained in the second reagent container, when determined to switch from the first reagent container to the second reagent container; determining whether or not an analysis result of the quality control measurement sample meets a predetermined condition; and controlling the measurement unit so as to start the aspiration of the next sample and to measure a measurement sample prepared from the next sample and the reagent contained in the second reagent container, when the analysis result of the quality control measurement sample meets the predetermined condition.

A third aspect of the present invention is a sample analyzing method comprising processes of: (a) starting successive measurement of a plurality of samples by a measurement unit; (b) determining whether or not to switch from a first reagent container to a second reagent container, each of which contains a same kind of reagent, while the measurement unit is performing the successive measurement by using the reagent contained in the first reagent container; (c) suspending a start of aspiration of a next sample, aspirating a quality control sample, and measuring a quality control measurement sample prepared from the quality control sample and the reagent contained in the second reagent container by the measurement unit, when determined to switch from the first reagent container to the second reagent container; and (d) starting the aspiration of the next sample by the measurement unit, when an analysis result of the quality control measurement sample meets a predetermined condition.

A fourth aspect of the present invention is a computer program product comprising: a computer readable medium, and software instructions, on the computer readable medium, for enabling a computer to perform predetermined operations comprising: receiving a start instruction to start successive measurement of a plurality of samples; controlling a measurement unit so as to start the successive measurement of the plurality of samples according to the reception of the start instruction; determining whether or not to switch from a first reagent container to a second reagent container, each of which contains a same kind of reagent, while the measurement unit is performing the successive measurement by using the reagent contained in the first reagent container; controlling the measurement unit so as to suspend a start of aspiration of a next sample, to aspirate a quality control sample, and to measure a quality control measurement sample prepared from the quality control sample and the reagent contained in the second reagent container, when determined to switch from the first reagent container to the second reagent container; and controlling the measurement unit so as to start the aspiration of the next sample when an analysis result of the quality control measurement sample meets a predetermined condition.

BRIEF DESCRIPTION OF THE DRAWINGS

FIG. 3 is a block diagram showing a schematic configuration of a drive section of the analyzer according to the first embodiment of the present invention;

FIG. 9 illustrates an example of a quality control information setting screen for receiving settings of information for quality control;

DETAILED DESCRIPTION OF THE EMBODIMENT

Hereinafter, with reference to the accompanying drawings, specific description is given on an analyzer according to embodiments of the present invention, by using an exemplary case where optical measurement and analysis are performed regarding the quantity, the degree of activity and the like of a specific substance related to coagulative and fibrinolytic functions of blood.

First Embodiment

Figure 1:
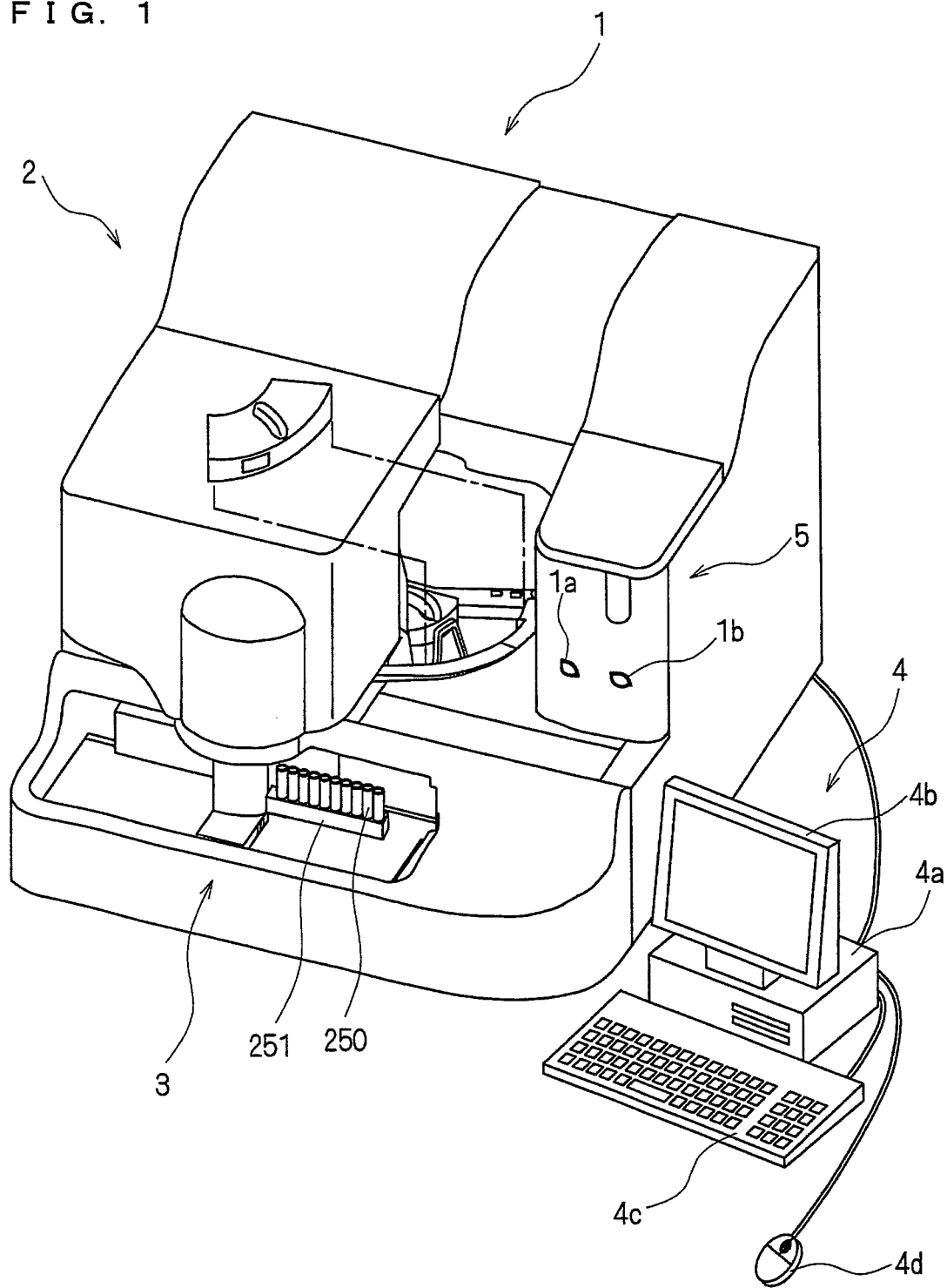
FIG. 1 is a perspective view showing an overall structure of an analyzer according to a first embodiment of the present invention.

FIG. 1 is a perspective view showing an overall structure of an analyzer according to a first embodiment of the present invention. As shown in FIG. 1, an analyzer 1 according to the present first embodiment includes a measurement mechanism section (measurement unit) 2, a sample transporting mechanism section 3 disposed in front of the measurement mechanism section 2, and a control apparatus 4 electrically connected to the measurement mechanism section 2. The measurement mechanism section 2 is provided with a sample container feeding section 5, into which sample containers each containing a sample to be measured are fed.

On the front face of the sample container feeding section 5, an emergency stop button 1a and a measurement start button 1b are provided. The emergency stop button 1a has a function to stop the measurement in case of emergency. The measurement start button 1b has a function to start the measurement. Note that the measurement can also be started or stopped by operating the control apparatus 4.

Figure 2:
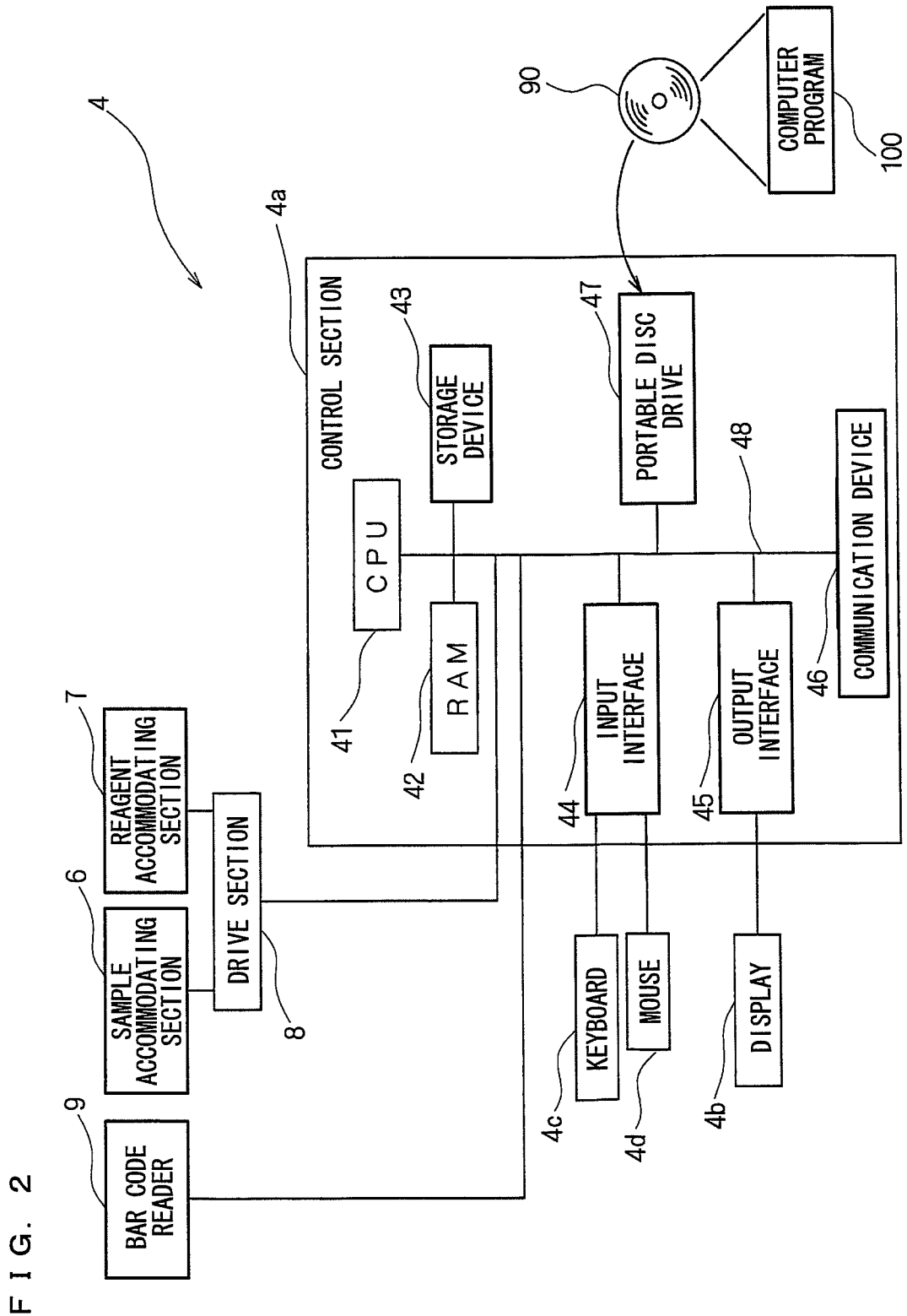
FIG. 2 is a block diagram showing a configuration of a control section of the analyzer according to the first embodiment of the present invention.

The control apparatus 4 is, for example, a personal computer and includes a control section 4a, a display 4b, a keyboard 4c, and a mouse 4d. FIG. 2 is a block diagram showing a configuration of the control section 4a of the analyzer 1 according to the first embodiment of the present invention.

The control section 4a includes at least a CPU (Central Processing Unit) 41, a RAM 42, a storage device 43, an input interface 44, an output interface 45, a communication device 46, a portable disc drive 47, and an internal bus 48 that connects these hardware components. The CPU 41 is connected, via the internal bus 48, to the hardware components of the control section 4a. The CPU 41 controls the operation of each of the above hardware components. The CPU 41 also controls operations of a drive section 8 and a bar code reader 9 that are described below, in accordance with a computer program 100 stored in the storage device 43.

The RAM 42 is structured as a volatile memory, such as an SRAM or a flash memory. To the RAM 42, a load module is loaded at the execution of the computer program 100. The RAM 42 stores temporary data and the like that are generated at the execution of the computer program 100.

The storage device 43 is structured as a stationary storage device (hard disk) or the like that is incorporated in the control section 4a. The computer program 100 is downloaded by the portable disc drive 47 from the portable storage medium 90, such as a DVD, a CD-ROM or the like, that stores information, such as programs, data, and the like. The computer program 100 is then stored in the storage device 43. The computer program 100 is, upon the execution thereof, loaded from the storage device 43 to the RAM 42 so as to be executed. It is needless to say that the computer program 100 may be downloaded via the communication device 46 from an external computer.

The communication device 46 is connected to the internal bus 48. The communication device 46 is capable of receiving/transmitting data from/to an external computer or the like, by being connected to an external network, such as the Internet, a LAN, or a WAN. For example, the storage device 43 described above is not limited to the one that is incorporated in the control section 4a. The storage device 43 may be an external storage medium, such as an external storage or the like, which is connected to the control section 4a via the communication device 46.

The input interface 44 is connected to data input devices, such as the keyboard 4c and the mouse 4d. The output interface 45 is connected to the display 4b, such as a CRT monitor or LCD, a printer, such as a laser or ink-jet printer, and the like.

The analyzer 1 is provided with a sample accommodating section 6 for accommodating sample containers and a reagent accommodating section 7 for accommodating reagent containers.

The sample accommodating section 6 and the reagent accommodating section 7 are configured to be movable through operation of the drive section 8. The operation of the drive section 8 is controlled by the control section 4a. The measurement mechanism section 2 is provided with the bar code reader 9 for reading information contained in bar code labels that are affixed to the sample containers accommodated in the sample accommodating section 6, the reagent containers accommodated in the reagent accommodating section 7, and the like.

The drive section 8 moves the sample accommodating section 6 and the reagent accommodating section 7, using stepping motors of a constant current drive type. The operation of the drive section 8 and the operation of the bar code reader 9 are controlled by the control section 4a connected thereto with signal wires.

FIG. 3 is a block diagram showing a schematic configuration of the drive section 8 of the analyzer 1 according to the first embodiment of the present invention. As shown in FIG. 3, upon reception of actuating signals from the CPU 41 of the control section 4a, a PPMC (pulse oscillator) 81 converts the actuating signals into command pulse signals, and transmits the command pulse signals to a motor driver 82. Upon reception of the command pulse signals, the motor driver 82 rotates a stepping motor 83 in accordance with the number of pulses of the command pulse signals.

For example, when the command pulse signals are control signals for controlling a rotation direction, the rotation direction of the stepping motor 83 is determined in accordance with a digital value "1" or "0" that indicates the rotation direction. The rotational speed of the stepping motor 83 can be changed in accordance with the frequency of the command pulse signals.

Figure 4:
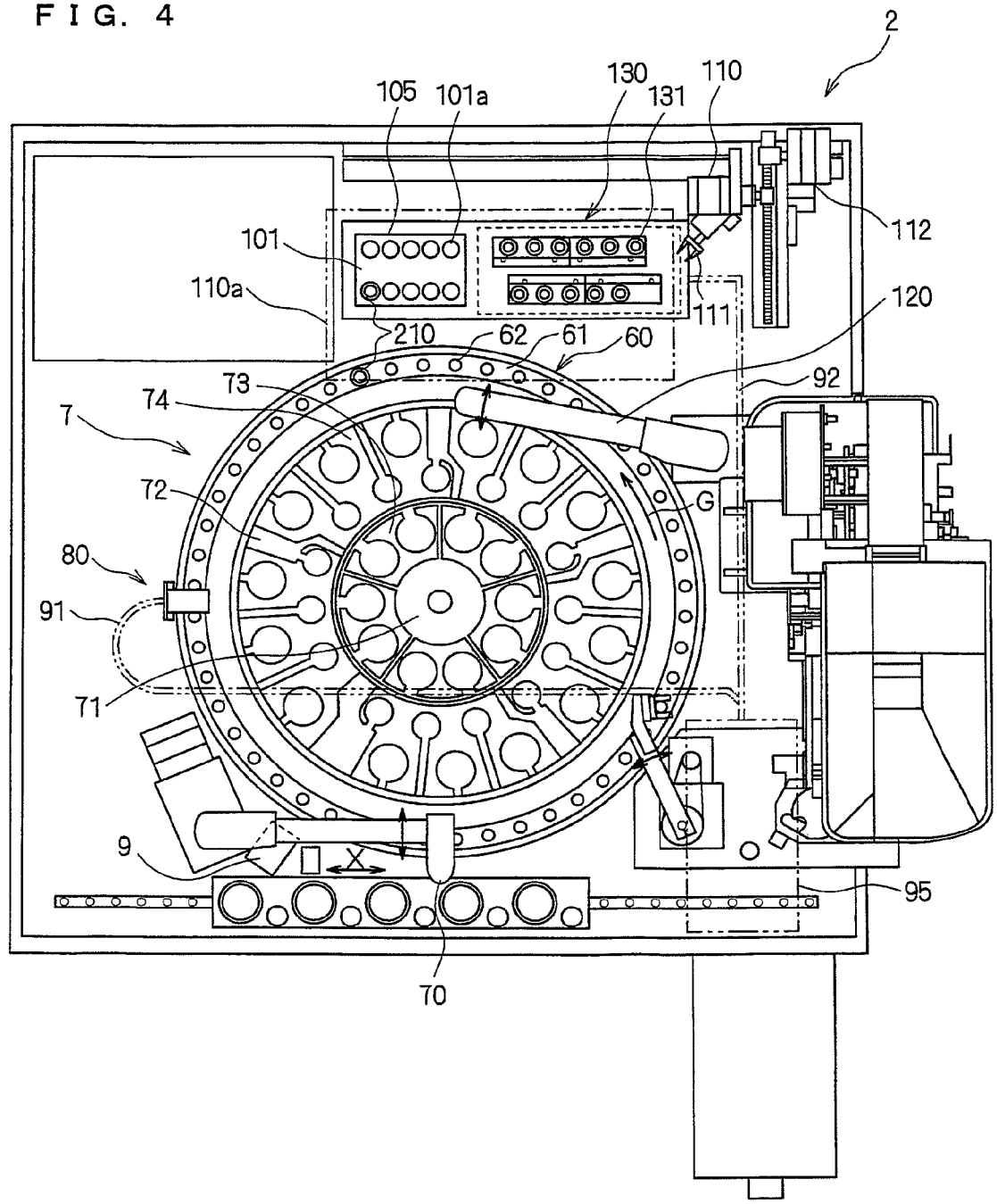
FIG. 4 is a partial plan view showing a schematic structure of the analyzer according to the first embodiment of the present invention.

FIG. 4 is a partial plan view showing a schematic structure of the analyzer 1 according to the first embodiment of the present invention. In the present first embodiment, the reagent accommodating section 7 includes a round-shaped first table 71 and an annular-shaped second table 72. The first table 71 holds a plurality of first container racks 73 each capable of accommodating reagent containers. The second table 72 holds a plurality of second container racks 74 each capable of accommodating reagent containers. The drive section 8 has a first stepping motor for rotating the first table 71, and a second stepping motor for rotating the second table 72. That is, the drive section 8 is configured to have a plurality of motor drivers 82, 82, and a plurality of stepping motors 83, 83.

When actuating signals are transmitted from the CPU 41 of the control section 4a, the stepping motors 83 operate in accordance with the command pulse signals converted in the drive section 8, respectively, and rotate the first table 71 and the second table 72, respectively. The drive section 8 is capable of rotating the first table 71 and the second table 72, independently of each other, in both the clockwise direction and the counterclockwise direction.

The first table 71 and the second table 72 are configured to be able to hold, in a detachable manner, the first container racks 73 and the second container racks 74, respectively. Each of the first container racks 73 and the second container racks 74 serves as a reagent container holder that accommodates and holds reagent containers. A bar code label, on which bar code information is printed, is affixed to each of the first container racks 73 and the second container racks 74. In order to read the affixed bar code label, the bar code reader 9 is provided near the side face of the second table 72, in such a manner as to have a predetermined distance from the second table 72. The bar code reader 9 is also connected to the control section 4a in such a manner as to allow data communication therebetween. For example, the read bar code information is converted into pulse signals to be transmitted to the CPU 41.

Figure 5:
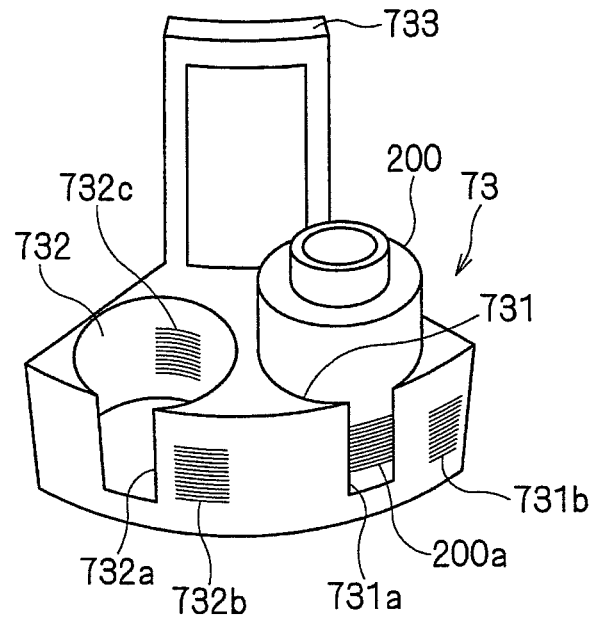
FIG. 5 is a perspective view showing a structure of a first container rack.

FIG. 5 is a perspective view showing a structure of the first container rack 73. The first container rack 73 includes two holders 731 and 732 for holding reagent containers 200, respectively; notches 731a and 732a provided at the front side of the holders 731 and 732, respectively; and a grip portion 733 formed so as to protrude upwards. The portion, for accommodating a reagent container 200, of each of the holders 731 and 732 is of a substantially circle shape, when viewed from above, so as to be able to hold a reagent container 200 that is of a cylindrical shape. In the case of a reagent container 200 having a smaller outer diameter than the inner diameter of the holders 731 and 732, such reagent containers can be held by the holders 731 and 732 in a stable manner, via adapters or the like, respectively.

To the outer periphery surfaces of the holders 731 and 732, bar code labels 731b and 732b are affixed, respectively. Also, to the inner periphery surfaces of the holders 731 and 732, bar code labels 731c and 732c are affixed, respectively. For example, when a reagent container 200 is held by the holder 731 of the first container rack 73, the bar code reader 9 cannot read the bar code label 731c affixed to the inner periphery surface of the holder 731.

Accordingly, in a case where, after reading the bar code label 731b, the bar code reader 9 has read the bar code label 200a affixed to the reagent container 200 without reading the bar code label 731c, the CPU 41 of the control section 4a can determine that the reagent container 200 containing a reagent corresponding to the bar code information read from the bar code label 200a is held by the holder 731.

Figure 6:
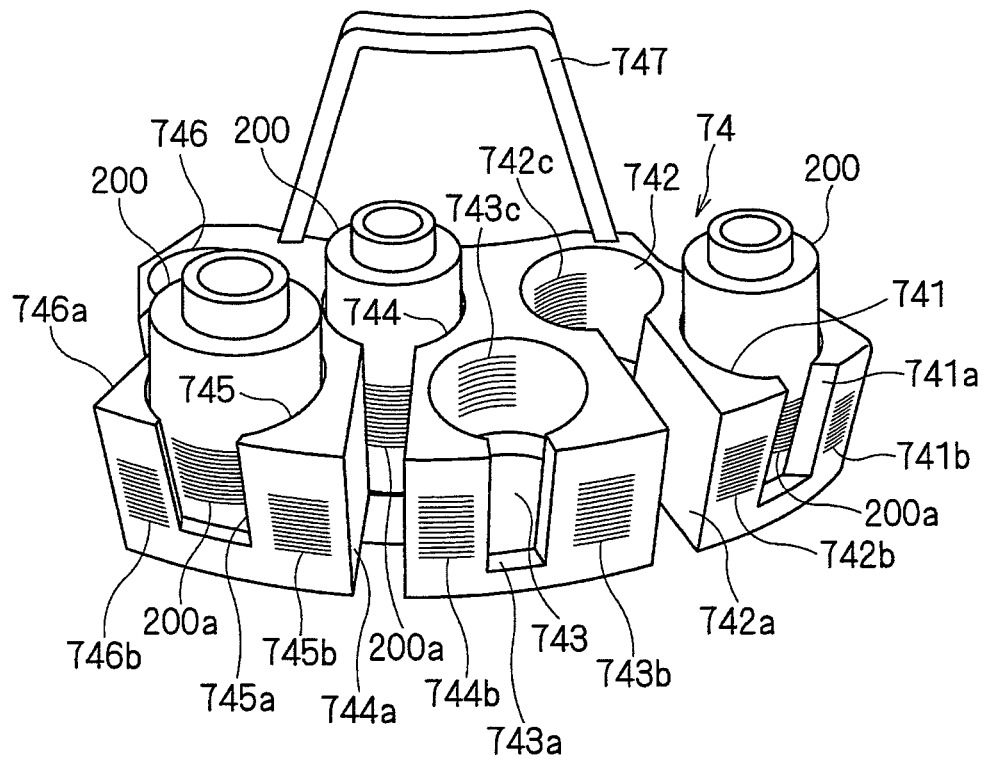
FIG. 6 is a perspective view showing a structure of a second container rack.

FIG. 6 is a perspective view showing a structure of the second container rack 74. The second container rack 74 includes six holders 741 to 746 for holding reagent containers 200, respectively; notches 741a to 746a provided at the front side of the holders 741 to 746, respectively; and a grip portion 747 formed so as to protrude upwards. The portion, for accommodating a reagent container 200, of each of the holders 741 to 746 is of a substantially circle shape, when viewed from above, so as to be able to hold a reagent container 200 that is of a cylindrical shape. In the case of a reagent container 200 having a smaller outer diameter than the inner diameter of the holders 741 to 746, such reagent containers can be held by the holders 741 to 746 in a stable manner, via adapters or the like, respectively.

To the outer periphery surfaces of the holders 741 to 746, bar code labels 741b to 746b are affixed, respectively. Also, to the inner periphery surfaces of the holders 741 to 746, bar code labels 741c to 746c are affixed, respectively. For example, when three reagent containers 200 are held by the holders 741, 744, and 745 of the second container rack 74, the bar code reader 9 cannot read the bar code labels 741c, 744c, and 745c affixed to the inner periphery surfaces of the holders 741, 744, and 745, respectively.

Accordingly, in a case where, after reading the bar code labels 741b, 744b, and 745b, the bar code reader 9 has read the bar code labels 200a that are affixed to the reagent containers 200 without reading the bar code labels 741c, 744c, and 745c, the CPU 41 of the control section 4a can determine that the reagent containers 200 containing reagents corresponding to the bar code information read from the bar code labels 200a are held by the holders 741, 744, and 745.

With reference back to FIG. 4, the measurement mechanism section 2 includes a sample container transporting section 60, a sample dispensing arm 70, a first optical information obtaining section 80, a lamp unit 95, a heating section 105, a sample container transferring section 110, a reagent dispensing arm 120, and a second optical information obtaining section 130. The sample dispensing arm 70 is caused to rotate, ascend, and descend by a stepping motor not shown so as to aspirate a sample contained in a test tube 250 (see FIG. 1) transported to a predetermined aspirating position by the sample transporting mechanism section 3, and so as to dispense the aspirated sample into a sample container 210 held by a sample container holder 62 of a sample container transporting table 61. The reagent dispensing arm 120 is caused to rotate, ascend, and descend by a stepping motor not shown so as to dispense a reagent accommodated in the reagent accommodating section 7 into the sample container 210 described above. In this manner, a measurement sample is prepared.

Figure 7:
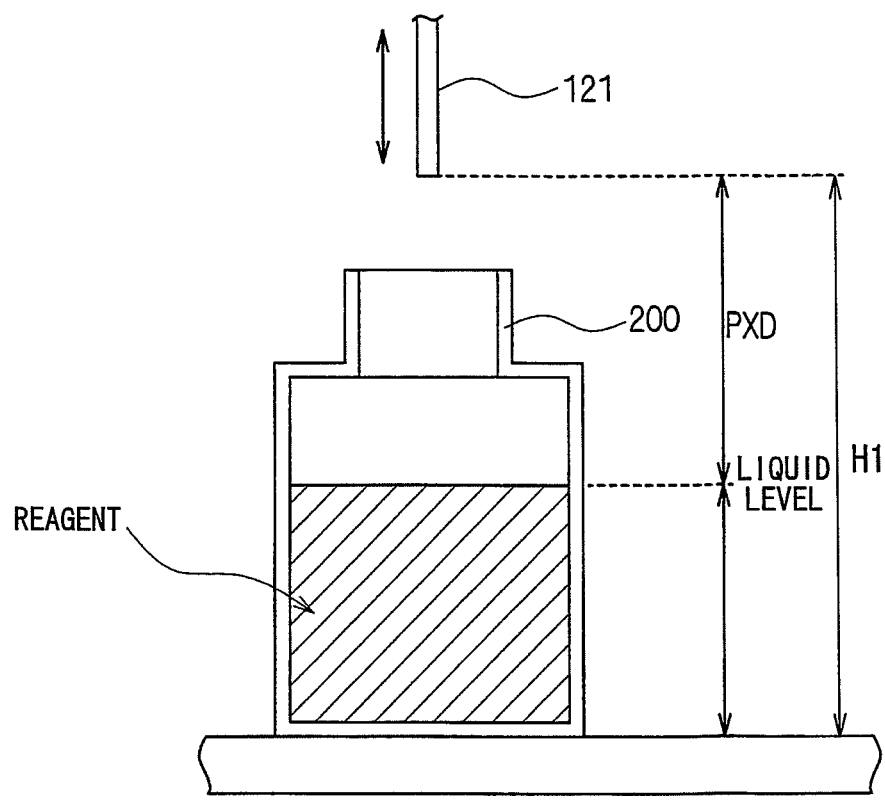
FIG. 7 illustrates a method of calculating a remaining amount of a reagent.

A pipette part is provided in the lower part of the reagent dispensing arm 120. The pipette part is inserted into a reagent container 200 in accordance with the ascending and descending motions of the reagent dispensing arm 120 caused by the stepping motor, so as to aspirate the reagent contained therein. At the time of aspiration of the reagent, the liquid level of the reagent is detected by a liquid level sensor provided at the tip of the pipette part, and a remaining amount of the reagent is calculated. FIG. 7 illustrates a method of calculating the remaining amount of the reagent.

The pipette part 121 of the reagent dispensing arm 120 moves downward from an initial position (height H1) at which a reagent aspirating operation is started. The pipette part 121 moves by a moving distance D each time a unit pulse is inputted to the stepping motor. Accordingly, a downward moving distance P×D of the pipette part 121 can be determined by using the number of pulses P inputted into the stepping motor. Then, the liquid level of the reagent is detected by the liquid level sensor provided at the tip of the pipette part 121. To be specific, the number of pulses P is obtained at the time when the liquid level sensor provided at the tip of the pipette part 121 has detected the liquid level of the reagent, whereby the downward moving distance P×D from the initial position H1 can be determined.

The number of pulses P, which has been obtained at the time when the liquid level of the reagent has been detected by the liquid level sensor and which has been inputted into the stepping motor, and the moving distance D per unit pulse of the pipette part 121 are transmitted to the control section 4a. The control section 4a calculates a remaining amount T of the reagent, using an internal area S, in the horizontal direction, of the reagent container 200. First, the control section 4a calculates the height H of the liquid level, by using (formula 1).

$$H = H1 - P \times D \quad \text{(formula 1)}$$

Next, by using (formula 2), the control section 4a calculates the remaining amount T of the reagent, based on the stored internal area S of the reagent container 200 and the calculated height H of the liquid level of the reagent.

$$T = H \times S \quad \text{(formula 2)}$$

Once the remaining amount T of the reagent has been obtained, it is possible to calculate the remaining number of times of measurement that can be performed on a predetermined measurement item by using the reagent. Accordingly, it is possible to determine whether or not it is necessary to change the reagent container 200 from which the pipette part 121 aspirates the reagent, whether or not it is necessary to replace the reagent container 200, or the like. Accordingly, it is possible to specify a timing at which a reagent for quality control is aspirated.

With reference back to FIG. 4, the measurement mechanism section 2 performs optical measurement on a sample supplied from the sample transporting mechanism section 3 shown in FIG. 1, so as to obtain optical information about the supplied sample. In the present first embodiment, optical measurement is performed on a sample that has been dispensed, into a sample container 210 in the measurement mechanism section 2, from a test tube 250 mounted on a rack 251 in the sample transporting mechanism section 3 shown in FIG. 1.

The sample container 210 containing the sample dispensed by the sample dispensing arm 70 is transported in the analyzer 1 by the sample container transporting section 60. The sample container transporting section 60 includes the annular-shaped sample container transporting table 61 arranged outside the annular-shaped second table 72; and a plurality of cylindrical sample container holders 62 that are circumferentially arranged, with predetermined intervals therebetween, on the sample container transporting table 61. Each sample container holder 62 holds one sample container 210.

The first optical information obtaining section 80 obtains optical information from the sample in order to measure presence/absence, density, and the like of interference substances (chyle, hemoglobin and bilirubin) in the sample before a reagent is added thereto. The first optical information obtaining section 80 obtains optical information (information obtained from light transmitted through the sample) from the sample in the sample container 210 that is held by a sample container holder 62 of the sample container transporting table 61. The first optical information obtaining section 80 is electrically connected to the control section 4a of the control apparatus 4, and transmits data obtained at the first optical information obtaining section 80 to the control section 4a of the control apparatus 4. Accordingly, in the control apparatus 4, the data obtained at the first optical information obtaining section 80 can be analyzed. Then, the absorbance, of the sample in the sample container 210, of five kinds of light emitted from a bifurcated optical fiber 91 is determined. In this manner, the presence/absence, the density and the like of the interference substances in the sample are analyzed. Based on the presence/absence, the density and the like of the interference substances in the sample, it is determined whether or not to analyze the optical information measured at the second optical information obtaining section 130.

The lamp unit 95 supplies light of five kinds of wavelengths (340 nm, 405 nm, 575 nm, 660 nm, and 800 nm) to be used in the optical measurement performed by the first optical information obtaining section 80 and by the second optical information obtaining section 130. That is, the lamp unit 95, which is a single lamp unit, is used for both the first optical information obtaining section 80 and the second optical information obtaining section 130. The light from the lamp unit 95 is supplied to the first optical information obtaining section 80 and the second optical information obtaining section 130 through the bifurcated optical fiber 91 and a bifurcated optical fiber 92, respectively.

The second optical information obtaining section 130 performs optical measurement (main measurement) on, under a plurality of conditions, a measurement sample contained in the sample container 210, by means of a detector that is disposed under a measurement sample mounting section 131 for mounting prepared measurement samples. The second optical information obtaining section 130 is also electrically connected to the control section 4a of the control apparatus 4, and transmits obtained data (optical information) to the control section 4a of the control apparatus 4. Accordingly, in the control apparatus 4, the data (optical information) transmitted from the second optical information obtaining section 130 is analyzed, based on an analysis result of the data (optical information) that has previously been obtained from the first optical information obtaining section 80. The analysis result is displayed on the display 4b.

The wavelength of 660 nm of the light emitted from the bifurcated optical fiber 92 is a main wavelength that is used to measure Fbg (amount of fibrinogen), PT (prothrombin time), and APTT (activated partial thromboplastin time). The wavelength of 800 nm of the light emitted from the bifurcated optical fiber 92 is a sub wavelength that is used to measure Fbg, PT, and APTT. The measurement wavelength for ATIII, which is a measurement item for a synthetic substrate method, is 405 nm. The measurement wavelength for D-dimer and FDP, which are measurement items for immunonephelometry, is 800 nm. The measurement wavelength for platelet aggregation is 575 nm.

The heating section 105 includes a plate 101 that can be kept warm, and is provided with ten sample container holders 101a each having a recessed shape. Each sample container holder 101a is capable of holding one sample container 210, and heats a sample having been dispensed into a sample container 210 to approximately 37° C., by holding the sample container 210 for a few minutes. To each sample heated in the heating section 105, a reagent is dispensed and measurement of the samples is performed, within a predetermined period of time after the heating is ended. Accordingly, it is possible to suppress alternation of the samples and of measurement samples prepared from the samples and reagents. Also, it is possible to stabilize measurement data.

The sample container transferring section 110 transfers sample containers 210 among the sample container transporting section 60, the heating section 105, and the second optical information obtaining section 130. The sample container transferring section 110 includes a transfer catcher 111 for holding a sample container 210, and a drive section 112 for moving the transfer catcher 111. The transfer catcher 111 is movable within a predetermined area by being driven by the drive section 112. The transfer catcher 111 transfers a sample container 210 among the sample container transporting section 60, the heating section 105, and the measurement sample mounting section 131 of the second optical information obtaining section 130.

The analysis process performed in the analyzer 1 having the above-described configuration will be described in detail.

In a conventional analyzer, when quality control is performed, a quality control sample is aspirated, a measurement sample for quality control (hereinafter referred to as a quality control measurement sample) is prepared, and then an analysis process is performed. Until an analysis result thereof is obtained, other analysis processes are not stopped. That is, analysis processes being performed on other samples are continued by using the reagent contained in another reagent container. Therefore, when the analysis result on the quality control sample is determined to be abnormal, it is necessary to perform the analysis process again on the samples that have been analyzed using the reagent suspected of deterioration and the like.

In such a case, the samples into which the reagent suspected of deterioration and the like has been dispensed from the reagent container 200 cannot be used any more, and thus, have to be disposed of. Therefore, it is possible to avoid consuming the samples in vain, by stopping the aspiration of samples while the analysis process is being performed on a quality control sample, and by resuming the aspiration of samples upon determination that the reagent has not deteriorated.

Figure 8:
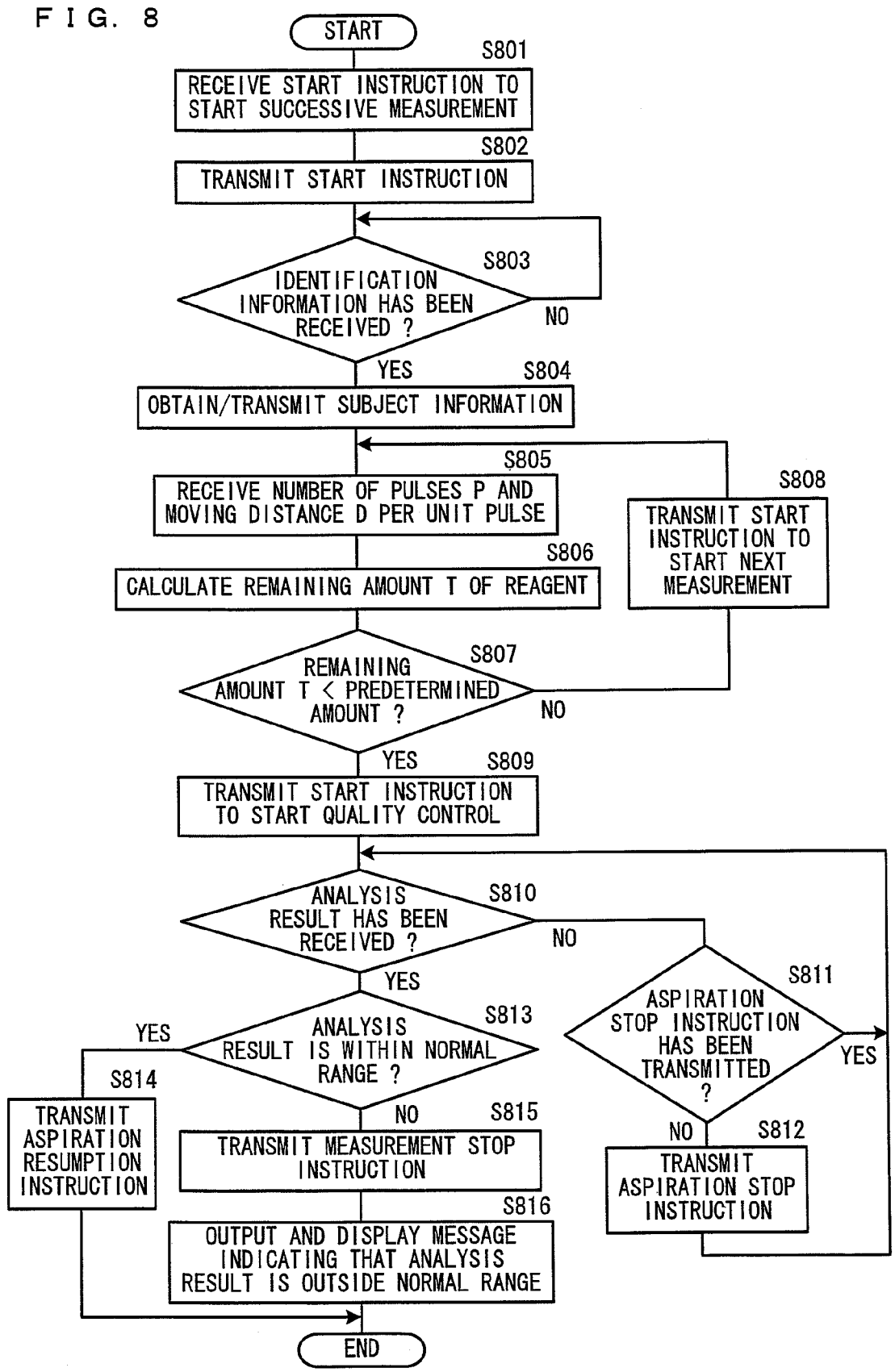
FIG. 8 is a flowchart showing process steps performed by a CPU of the control section of the analyzer according to the first embodiment of the present invention.

FIG. 8 is a flowchart showing process steps performed by the CPU 41 of the control section 4a of the analyzer 1 according to the first embodiment of the present invention. The CPU 41 of the control section 4a receives a start instruction to start successive measurement of a plurality of samples (step S801). Although the manner of receiving the start instruction is not limited in particular, the start instruction is received through a clicking operation of the mouse 4d or the like performed onto a start instruction button displayed on a menu screen.

The CPU 41 transmits the start instruction to start the successive measurement to the measurement mechanism section (measurement unit) 2 (step S802). Upon reception of the start instruction, the measurement mechanism section 2 causes a bar code reader (not shown) to read a bar code label (not shown) affixed to each test tube 250 containing a sample, obtains identification information (sample ID) of the sample, and transmits the identification information to the CPU 41 of the control section 4a.

The CPU 41 of the control section 4a determines whether or not the identification information (sample ID) has been received (step S803). When the CPU 41 has determined that the identification information (sample ID) has not been received (step S803: NO), the CPU 41 enters a reception waiting state. When the CPU 41 has determined that the identification information (sample ID) has been received (step S803: YES), the CPU 41 inquires of the storage device 43, obtains subject information that has been stored therein, and transmits the subject information to the measurement mechanism section 2 (step S804). In this manner, it is possible to specify measurement items of a sample to be measured.

Upon reception of the subject information, the measurement mechanism section 2 aspirates a sample to be measured of the subject, and aspirates a reagent to be used for the measurement by means of the pipette part 121 of the reagent dispensing arm 120. At the time when the liquid level sensor provided at the tip of the pipette part 121 has detected the liquid level of the reagent, the measurement mechanism section 2 transmits to the control section 4a the number of pulses P and the moving distance D per unit pulse of the pipette part 121.

The CPU 41 of the control section 4a receives the number of pulses P and the moving distance D per unit pulse of the pipette part 121 (step S805). The CPU 41 reads the internal area S, in the horizontal direction, of the reagent container 200. The internal area S has been stored in the storage device 43. The CPU 41 calculates the height H of the liquid level, using (formula 1).

$$H = H1 - P \times D \qquad \text{(formula 1)}$$

The CPU 41 calculates a remaining amount T of the reagent by using (formula 2), based on the read internal area S of the reagent container 200 and the calculated height H of the liquid level of the reagent (step S806).

$$T = H \times S \qquad \text{(formula 2)}$$

The CPU 41 determines whether or not the remaining amount T of the reagent contained in the reagent container 200 has become less than a predetermined amount (step S807). When the CPU 41 has determined that the remaining amount T of the reagent is equal to or greater than the predetermined amount (step S807: NO), the CPU 41 transmits a start instruction to start the next measurement to the measurement mechanism section 2 (step S808), and returns the processing to step S805 to repeat the above described processes. When the CPU 41 has determined that the remaining amount T of the reagent has become less than the predetermined amount (step S807: YES), the CPU 41 transmits a start instruction to start quality control to the measurement mechanism section 2 (step S809). Upon reception of the start instruction to start quality control, the measurement mechanism section 2 aspirates a quality control sample, mixes the quality control sample with the reagent contained in another reagent container 200, thereby preparing a quality control measurement sample, starts measurement, and transmits to the control section 4a an analysis result based on measurement data.

Note that the predetermined amount to be used as a criterion for the determination of the remaining amount T is not limited in particular. For example, the predetermined amount may be a reagent amount that is necessary to perform measurement once for a measurement item that consumes a greatest amount from the reagent. In such a case, when it is determined that the remaining amount of the reagent in the reagent container 200 has become less than the above reagent amount necessary to perform measurement once, the analyzer 1 causes the measurement mechanism section 2 to aspirate a quality control sample, and to mix the quality control sample with the reagent contained in another reagent container 200 to prepare a quality control measurement sample. Then, the analyzer 1 obtains an analysis result of the quality control measurement sample. In this manner, it is possible to use the reagent in the reagent container 200 to the maximum extent possible until the above-described reagent amount necessary to perform measurement once no longer remains in the reagent container 200.

Alternatively, it may be set for each measurement item of a sample whether or not to perform measurement of a quality control sample and suspension of measurement of the next sample when it is determined that the remaining amount of the reagent in the currently used reagent container 200 has become less than a predetermined amount. That is, the following configuration may be employed: when the remaining amount of the reagent in the reagent container 200 has become less than the predetermined amount, and when the measurement item of the next sample is a predetermined measurement item, measurement of a quality control sample and suspension of measurement of the next sample are performed; meanwhile, even when the remaining amount of the reagent in the reagent container 200 has become less than the predetermined amount, if the measurement item of the next sample is not the predetermined measurement item, then, measurement of a quality control sample and suspension of measurement of the next sample are not performed. This configuration is possible because, since different measurement items have different amounts of the reagent necessary to perform measurement thereon, it is expected that a remaining reagent amount that is not sufficient for one measurement item may be sufficient for another measurement item.

FIG. 9 illustrates an example of a quality control information setting screen for receiving settings of information for quality control. As shown in FIG. 9, the measurement items of a sample are listed in a measurement item display area 901.

Each measurement item displayed in the measurement item display area 901 has a plurality of setting parameters. The plurality of setting parameters are listed in a setting parameter display area 902.

Through a clicking operation of the mouse 4d, the user selects "periodical automatic QC" or "vial QC" in a quality control setting area 903, for each item that is set for quality control. The "periodical automatic QC" is a setting for performing quality control automatically at a predetermined interval of time. The "vial QC" is a setting for performing quality control for each reagent container 200. In a case where selection of the "vial QC" is received, a quality control sample is aspirated when it is determined that the remaining amount of one reagent container 200 has become less than a predetermined amount.

With reference back to FIG. 8, the CPU 41 of the control section 4a determines whether or not an analysis result of the quality control measurement sample has been received (step S810). When the CPU 41 has determined that the analysis result of the quality control measurement sample has not been received (step S810: NO), the CPU 41 determines whether or not an aspiration stop instruction to stop sample aspiration has been transmitted to the measurement mechanism section 2. When an aspiration stop instruction has not been transmitted, the CPU 41 transmits an aspiration stop instruction to the measurement mechanism section 2 (step S812). When an aspiration stop instruction has been transmitted, the CPU 41 returns the processing to step S810 to repeat the above-described processes.

Upon reception of the aspiration stop instruction, the measurement mechanism section 2 stops the sample aspiration being performed by the sample dispensing arm 70. Accordingly, the sample aspiration can be stopped until the control section 4a determines that an analysis result of the quality control measurement sample has been obtained. Accordingly, even when deterioration and the like of the reagent are detected, it is possible to avoid, in advance, consuming the samples in vain.

When the CPU 41 has determined that an analysis result of the quality control measurement sample has been received (step S810: YES), the CPU 41 determines whether or not the received analysis result is within a normal range (step S813). Whether or not the analysis result is within the normal range may be determined based on, for example, whether or not the received analysis result is within an allowable range of an analysis result previously obtained on a quality control sample.

When the CPU 41 has determined that the received analysis result is within the normal range (step S813: YES), the CPU 41 transmits to the measurement mechanism section 2 an aspiration resumption instruction to resume the sample aspiration (step S814). This allows resumption of the measurement without the reagent container 200 being replaced, thereby eliminating the necessity of onerous work by the user.

When the CPU 41 has determined that the received analysis result is outside the normal range (step S813: NO), the CPU 41 transmits to the measurement mechanism section 2 a measurement stop instruction to stop the sample measurement (step S815), and displays on the display 4b a message indicating that the analysis result on the quality control sample is outside the normal range (step S816). In this manner, preparation of measurement samples by using the reagent suspected of deterioration and the like can be avoided in advance. Accordingly, it is possible to perform the analysis process properly by, for example, replacing the reagent container 200.

Note that the reagent container holder is capable of holding three or more reagent containers 200 each containing the same kind of reagent. When the CPU 41 of the control section 4a has determined that the analysis result of the quality control measurement sample is outside the normal range, the CPU 41 causes the measurement mechanism section 2 to aspirate a quality control sample again, and to mix the quality control sample with the reagent contained in another reagent container 200 to prepare a quality control measurement sample. Then, the CPU 41 obtains an analysis result of the quality control measurement sample. Accordingly, it is possible to perform quality control by using the reagent contained in this other reagent container 200, without replacing the currently used reagent container 200. In this manner, it is possible to perform quality control by using the reagent that can be used, without the user having to perform onerous work, for example, replacement of the reagent container 200.

As described above, according to the present first embodiment, when the analysis result of the quality control measurement sample has not been obtained, the sample aspiration can be stopped in the measurement mechanism section 2. Accordingly, the analysis process can be stopped until the analysis result on the quality control sample is obtained, and preparation of measurement samples by using the reagent suspected of deterioration and the like can be avoided in advance. Therefore, the samples are not consumed in vain, and quality control of the reagent can be performed properly.

Second Embodiment

The configuration of the analyzer 1 according to the second embodiment of the present invention is the same as that according to the first embodiment. Therefore, the same reference numerals are used, and the detailed description will be omitted. The present second embodiment differs from the first embodiment in that in the present second embodiment, transmission of an aspiration stop instruction to stop the sample aspiration is performed before an analysis result of the quality control sample is received.

The analysis process in the analyzer 1 according to the second embodiment is described in detail. In a conventional analyzer, when quality control is performed, a quality control sample is aspirated, a quality control measurement sample is prepared, and then an analysis process is performed. Until an analysis result thereof is obtained, other analysis processes are not stopped. That is, analysis processes being performed on other samples are continued by using the reagent contained in another reagent container. Therefore, when the analysis result on the quality control sample is determined to be abnormal, it is necessary to perform the analysis process again on the samples that have been analyzed using the reagent suspected of deterioration and the like.

In such a case, the samples into which the reagent suspected of deterioration and the like has been dispensed from the reagent container 200 cannot be used any more, and thus, have to be disposed of. Therefore, it is possible to avoid consuming the samples in vain, by causing the measurement unit to stop sample aspiration when it is determined that the remaining amount of one reagent container has become less than a predetermined amount, and by causing the measurement unit to resume the sample aspiration when it is determined, as a result of performing the quality control, that the reagent has not deteriorated.

Figure 10:
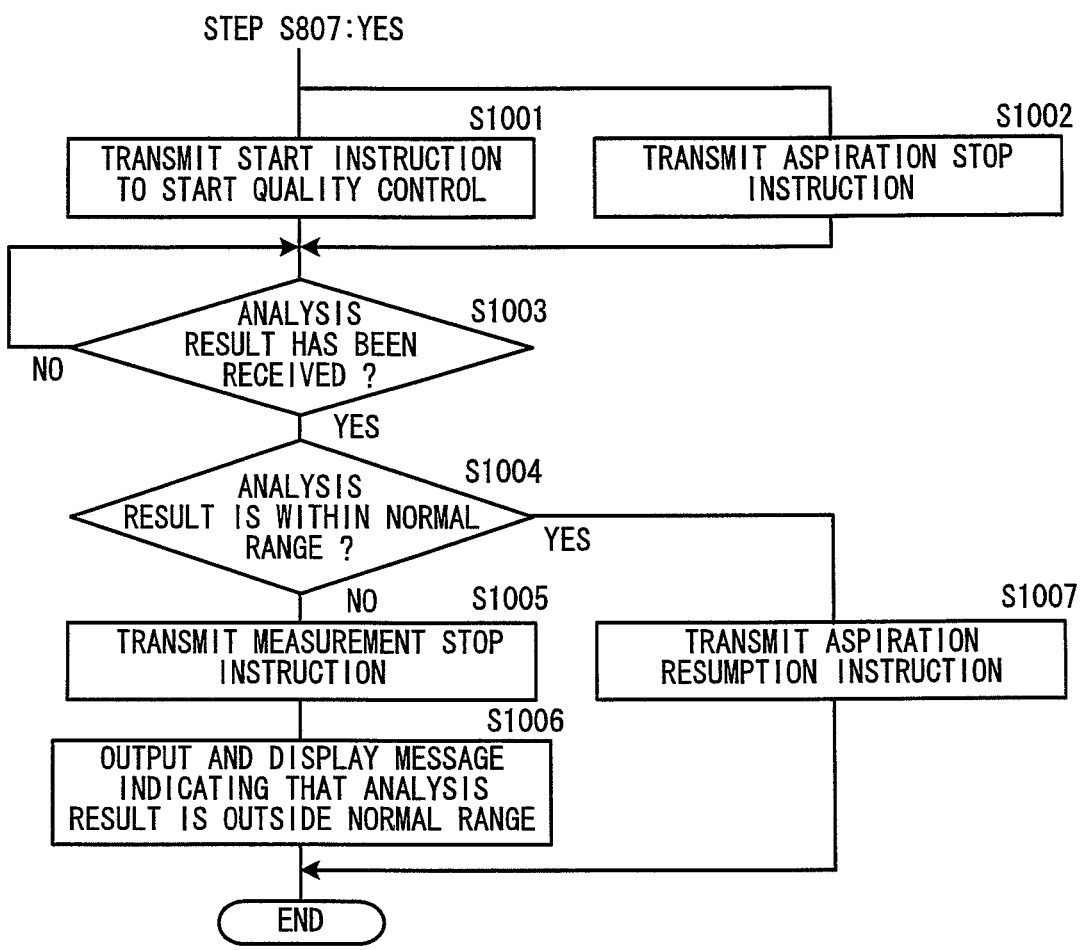
FIG. 10 is a flowchart showing process steps performed by the CPU of the control section of the analyzer according to a second embodiment of the present invention.

FIG. 10 is a flowchart showing process steps performed by the CPU 41 of the control section 4s of the analyzer 1 according to the second embodiment of the present invention. The CPU 41 of the control section 4a performs the processes from step S801 to step S807, as in the first embodiment. The CPU 41 determines whether or not the remaining amount T of the reagent in the reagent container 200 has become less than a predetermined amount (step S807). When the CPU 41 has determined that the remaining amount T of the reagent is equal to or greater than the predetermined amount (step S807: NO), the CPU 41 transmits a start instruction to start the next measurement to the measurement mechanism section 2 (step S808), and returns the processing to step S805 to repeat the above-described processes.

When the CPU 41 has determined that the remaining amount T of the reagent has become less than the predetermined amount (step S807: YES), the CPU 41 transmits to the measurement mechanism section 2 a start instruction to start quality control (step S1001), and also transmits to the measurement mechanism section 2 an aspiration stop instruction to stop the sample aspiration (step S1002). Upon reception of the start instruction to start quality control, the measurement mechanism section 2 aspirates a quality control sample, mixes the quality control sample with the reagent, thereby preparing a quality control measurement sample, starts measurement, and transmits to the control section 4a an analysis result based on measurement data. Upon reception of the aspiration stop instruction to stop the sample aspiration, the measurement mechanism section 2 stops the sample aspiration, and does not aspirate a new sample until receiving an aspiration resumption instruction.

Note that the predetermined amount to be used as a criterion for the determination of the remaining amount T is not limited in particular. For example, the predetermined amount may be the reagent amount necessary to perform measurement once. In such a case, when it is determined that the remaining amount of the reagent in the reagent container 200 has become less than the reagent amount necessary to perform measurement once, the measurement mechanism section 2 is caused to aspirate a quality control sample, and to mix the quality control sample with the reagent contained in another reagent container 200 to prepare a quality control measurement sample. Then, an analysis result of the quality control measurement sample is obtained. Accordingly, it is possible to shorten the time period from the time when the quality control measurement is performed on the reagent contained in this other reagent container 200, to the time when the reagent contained therein is used for the measurement of the sample. Accordingly, it is possible to avoid preparing a measurement sample in vain by using the reagent suspected of deterioration and the like.

Alternatively, it may be set for each measurement item of a sample whether or not to perform aspiration of a quality control sample when it is determined that the remaining amount of the reagent in the currently used reagent container 200 has become less than a predetermined amount. This is because, since different measurement items have different amounts of the reagent necessary to perform measurement thereon, it is expected that a remaining reagent amount that is not sufficient for one measurement item may be sufficient for another measurement item.

The CPU 41 determines whether or not an analysis result of the quality control measurement sample has been received (step S1003). When the CPU 41 has determined that an analysis result of the quality control measurement sample has not been received (step S1003: NO), the CPU 41 enters a reception waiting state. When the CPU 41 has determined that an analysis result of the quality control measurement sample has been received (step S1003: YES), the CPU 41 determines whether or not the received analysis result is within a normal range (step S1004). Whether or not the analysis result is within the normal range may be determined based on, for example, whether or not the received analysis result is within an allowable range of an analysis result previously obtained on a quality control sample.

When the CPU 41 has determined that the received analysis result is within the normal range (step S1004: YES), the CPU 41 transmits to the measurement mechanism section 2 an aspiration resumption instruction to resume the sample aspiration (step S1007). This allows resumption of the measurement without the reagent container 200 being replaced, thereby eliminating the necessity of onerous work by the user.

When the CPU 41 has determined that the received analysis result is outside the normal range (step S1004: NO), the CPU 41 transmits to the measurement mechanism section 2 a measurement stop instruction to stop the sample measurement (step S1005), and displays on the display 4b a message indicating that the analysis result on the quality control sample is outside the normal range (step S1006). In this manner, preparation of measurement samples by using the reagent suspected of deterioration and the like can be avoided in advance. Accordingly, it is possible to perform the analysis process properly by, for example, replacing the reagent container 200.

As described above, according to the present second embodiment, when it is determined that the remaining amount of the reagent in one reagent container has become less than a predetermined amount, the sample aspiration can be stopped irrespective of whether or not quality control has been performed. Accordingly, unnecessary sample aspiration can be prevented in advance, and quality control of the reagent can be performed properly.

Third Embodiment

The configuration of the analyzer 1 according to the third embodiment of the present invention is the same as that according to the first embodiment. Therefore, the same reference numerals are used, and the detailed description will be omitted. The present third embodiment differs from the first and second embodiments in that, in the present third embodiment, an aspiration instruction is transmitted for each sample.

The analysis process performed in the analyzer 1 according to the third embodiment is described in detail. In a conventional analyzer, when quality control is performed, a quality control sample is aspirated, a quality control measurement sample is prepared, and then an analysis process is performed. Until an analysis result thereof is obtained, other analysis processes are not stopped. That is, analysis processes being performed on other samples are continued by using the reagent contained in another reagent container. Therefore, when the analysis result on the quality control sample is determined to be abnormal, it is necessary to perform the analysis process again on the samples that have been analyzed using the reagent suspected of deterioration and the like.

Figure 11:
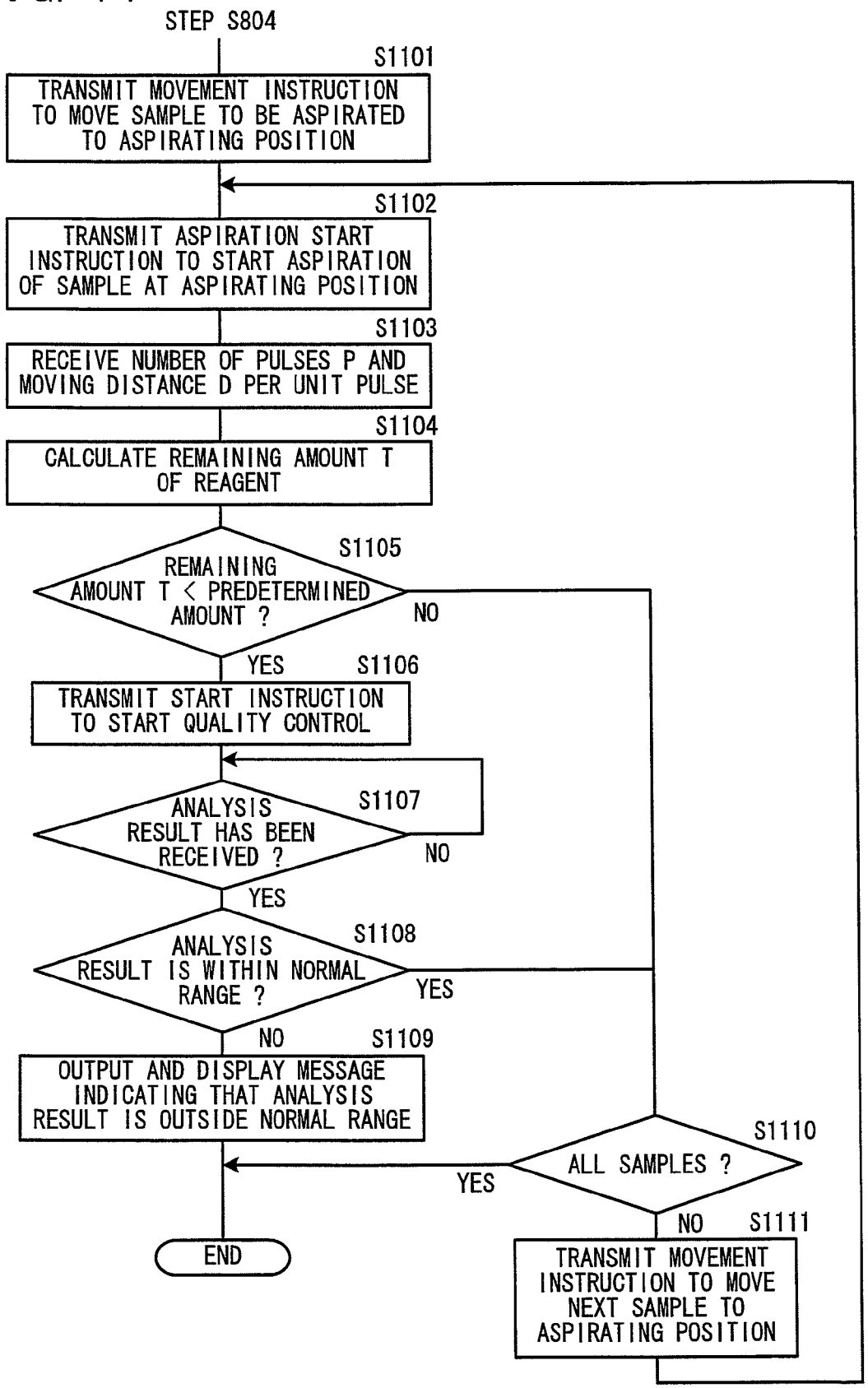
FIG. 11 is a flowchart showing process steps performed by the CPU of the control section of the analyzer according to a third embodiment of the present invention.

FIG. 11 is a flowchart showing process steps performed by the CPU 41 of the control section 4a of the analyzer 1 according to the third embodiment of the present invention. The CPU 41 of the control section 4a performs the processes from step S801 to step S804, as in the first embodiment. The CPU 41 inquires of the storage device 43, obtains subject information that has been stored therein, and transmits the subject information to the measurement mechanism section 2 (step S804).

The CPU 41 transmits to the measurement mechanism section 2 a movement instruction to move a test tube 250 to an aspirating position, the test tube 250 containing a sample to be aspirated, that is, the sample to be analyzed (step S1101). The CPU 41 transmits to the measurement mechanism section 2 an aspiration start instruction to start aspiration of the sample contained in the test tube 250 that has been moved to the aspirating position (step S1102).

Upon reception of the aspiration start instruction, the measurement mechanism section 2 starts the aspiration of the sample to be measured of the subject. The measurement mechanism section 2 aspirates a reagent to be used for the measurement by means of the pipette part 121 of the reagent dispensing arm 120. At the time when the liquid level sensor provided at the tip of the pipette part 121 has detected the liquid level of the reagent, the measurement mechanism section 2 transmits to the control section 4a the number of pulses P and the moving distance D per unit pulse of the pipette part 121.

The CPU 41 receives the number of pulses P and the moving distance D per unit pulse of the pipette part 121 (step S1103). The CPU 41 reads the internal area S, in the horizontal direction, of the reagent container 200. The internal area S has been stored in the storage device 43. The CPU 41 calculates the height H of the liquid level, using (formula 1).

$$H = H1 - P \times D \quad \text{(formula 1)}$$

The CPU 41 calculates a remaining amount T of the reagent by using (formula 2), based on the read internal area S of the reagent container 200 and the calculated height H of the liquid level of the reagent (step S1104).

$$T = H \times S \quad \text{(formula 2)}$$

The CPU 41 determines whether or not the remaining amount T of the reagent in the reagent container 200 has become less than a predetermined amount (step S1105). When the CPU 41 has determined that the remaining amount T of the reagent is less than the predetermined amount (step S1105: YES), the CPU 41 transmits to the measurement mechanism section 2 a start instruction to start quality control (step S1106). Upon reception of the start instruction to start quality control, the measurement mechanism section 2 aspirates a quality control sample, mixes the quality control sample with the reagent, thereby preparing a quality control measurement sample, starts measurement, and transmits to the control section 4a an analysis result based on measurement data.

Note that the predetermined amount to be used as a criterion for the determination of the remaining amount T is not limited in particular. For example, the predetermined amount may be the reagent amount necessary to perform measurement once. In such a case, when it is determined that the remaining amount of the reagent in the reagent container 200 has become less than the reagent amount necessary to perform measurement once, the measurement mechanism section 2 is caused to aspirate a quality control sample, and to mix the quality control sample with the reagent contained in another reagent container 200 to prepare a quality control measurement sample. Then, an analysis result of the quality control measurement sample is obtained. In this manner, it is possible to use the reagent in the reagent container 200 to the maximum extent possible until the reagent amount necessary to perform measurement once no longer remains in the reagent container 200.

Alternatively, it may be set for each measurement item of a sample whether or not to perform aspiration of a quality control sample when it is determined that the remaining amount of the reagent in the currently used reagent container 200 has become less than a predetermined amount. This is because, since different measurement items have different amounts of the reagent necessary to perform measurement thereon, it is expected that a remaining reagent amount that is not sufficient for one measurement item may be sufficient for another measurement item.

The CPU 41 determines whether or not an analysis result of the quality control measurement sample has been received (step S1107). When the CPU 41 has determined that an analysis result of the quality control measurement sample has not been received (step S1107: NO), the CPU 41 enters a reception waiting state. When the CPU 41 has determined that an analysis result of the quality control measurement sample has been received (step S1107: YES), the CPU 41 determines whether or not the received analysis result is within a normal range (step S1108). Whether or not the analysis result is within the normal range may be determined based on, for example, whether or not the received analysis result is within an allowable range of an analysis result previously obtained on a quality control sample.

When the CPU 41 has determined that the received analysis result is outside the normal range (step S1108: NO), the CPU 41 displays on the display 4*b* a message indicating that the analysis result on the quality control sample is outside the normal range (step S1109). Accordingly, preparation of measurement samples by using the reagent suspected of deterioration and the like can be avoided in advance. Accordingly, it is possible to perform the analysis process properly by, for example, replacing the reagent container 200.

When the CPU 41 has determined that the remaining amount T of the reagent is equal to or greater than the predetermined amount (step S1105: NO), the CPU 41 determines whether or not all the samples have been aspirated (step S1110). Also, when the CPU 41 has determined that the received analysis result is within the normal range (step S1108: YES), the CPU 41 determines whether or not all the samples have been aspirated (step S1110). When the CPU 41 determines that there are samples that have not been aspirated yet (step S1110: NO), the CPU 41 transmits to the measurement mechanism section 2 a movement instruction to move a test tube 250 containing the next sample to the aspirating position (step S1111). Then, the CPU 41 returns the processing to step S1102 to repeat the above-described processes. When the CPU 41 has determined that all the samples have been aspirated (step S1110: YES), the CPU 41 ends the processing.

As described above, according to the present third embodiment, whether or not it is necessary to perform quality control is determined for each sample. In a case where it is necessary to perform quality control, it is possible to cause the measurement unit to start aspiration of the next sample when an analysis result of a quality control measurement sample is within a normal range. Therefore, only when the analysis result on the quality control measurement sample is within the normal range, the aspiration of the next sample can be started. Accordingly, the samples are not consumed in vain, and quality control of the reagent can be performed properly.

The present invention is not limited to the embodiments described above. Numerous other modifications and replacements can be devised without departing from the scope of the present invention. For example, in the configurations described in the embodiments described above, the analyzer 1 can be operated by receiving designations, by means of the keyboard 4*c* or the mouse 4*d*, of the buttons and the like displayed on the screen. However, the present invention is not limited thereto. For example, the analyzer 1 may have a configuration in which a touch panel is employed in the display 4*b*, thereby allowing the analyzer 1 to be operated by a user directly touching the buttons and the like displayed on the screen.

Moreover, in the first to third embodiments described above, the CPU 41 is configured to transmit a start instruction to start quality control to the measurement mechanism section 2 when the CPU 41 has determined that the remaining amount T of the reagent has become less than a predetermined amount. However, the present invention is not limited thereto. For example, when the CPU 41 has determined that the expiration date of the reagent has expired based on the information contained in the reagent bar code read by the bar code reader 9, the CPU 41 may transmit a start instruction to start quality control to the measurement mechanism section 2.

Moreover, in the first to third embodiments described above, the CPU 41 is configured to transmit in step S811 an instruction to stop the aspiration of all the samples when the CPU 41 has determined in step S807 that the remaining amount T of the reagent has become less than the predetermined amount. However, the present invention is not limited thereto. For example, only the aspiration of a sample may be stopped whose measurement items require the reagent whose remaining amount T has become less than the predetermined amount; and the aspiration of a sample may be continued whose measurement items do not require the reagent. Accordingly, it is possible to enhance the sample processing capability when the quality control measurement is performed.

Moreover, in the first to third embodiments described above, when an analysis result on a quality control sample is within a normal range, the CPU 41 of the control section 4*a* transmits to the measurement mechanism section 2 an aspiration resumption instruction to resume the sample aspiration, and the measurement mechanism section 2 resumes the sample aspiration in accordance with the aspiration resumption instruction. However, the present invention is not limited thereto. For example, when the analysis result on the quality control sample is within the normal range, a message indicating that the analysis result on the quality control sample is within the normal range may be displayed on the display 4*b*; and when the CPU 41 has received an aspiration resumption instruction provided by the user, the aspiration resumption instruction may be transmitted to the measurement mechanism section 2.

What is claimed is:
1. A sample analyzer comprising:
a reagent container holder configured to hold a first reagent container and a second reagent container, each of which contains a same kind of reagent;
a measurement unit for aspirating a sample to be measured, and for measuring a measurement sample prepared from the sample and the reagent contained in the first reagent container or the second reagent container; and
an information processing unit configured to perform operations comprising:
receiving a start instruction to start successive measurement of a plurality of samples;
controlling the measurement unit to start the successive measurement of the plurality of samples according to the reception of the start instruction;
determining whether to switch from the first reagent container to the second reagent container while the measurement unit is performing the successive measurement by using the reagent contained in the first reagent container;
transmitting a start instruction to start quality control to the measurement unit and an aspiration stop instruction to stop sample aspiration when it is determined to switch from the first reagent container to the second reagent container;

controlling the measurement unit upon reception of the start instruction and the aspiration stop instruction to suspend a start of aspiration of a next sample, to aspirate a quality control sample, and to measure a quality control measurement sample prepared from the quality control sample and the reagent contained in the second reagent container; and controlling the measurement unit to start the aspiration of the next sample when an analysis result of the quality control measurement sample meets a predetermined condition, wherein both of the first reagent container and the second reagent container are held by the reagent container holder during suspension of the start of the aspiration of the next sample.

2. The sample analyzer of claim 1, wherein
the information processing unit controls the measurement unit to start the aspiration of the next sample when the analysis result of the quality control measurement sample is within a predetermined range.

3. The sample analyzer of claim 1, wherein
the information processing unit controls the measurement unit to measure a measurement sample prepared from the aspirated next sample and the reagent contained in the second reagent container.

4. The sample analyzer of claim 1, further comprising a display, wherein
the information processing unit controls the display to display a message indicating that the analysis result of the quality control measurement sample does not meet the predetermined condition when the analysis result of the quality control measurement sample does not meet the predetermined condition.

5. The sample analyzer of claim 1, wherein
the reagent container holder is configured to hold a third reagent container containing the same kind of reagent as the reagent contained in each of the first and the second reagent containers; and
the information processing unit controls the measurement unit to aspirate a quality control sample and to measure a quality control measurement sample prepared from the quality control sample and the reagent contained in the third reagent container, when the analysis result of the quality control measurement sample does not meet the predetermined condition.

6. The sample analyzer of claim 1, wherein
the operation of determining whether to switch from the first reagent container to the second reagent container comprises operations of:
obtaining a remaining amount of the reagent in the first reagent container;
determining whether the remaining amount of the reagent in the first reagent container is less than a predetermined amount; and
determining to switch from the first reagent container to the second reagent container when the remaining amount of the reagent in the first reagent container is less than the predetermined amount.

7. The sample analyzer of claim 6, wherein
the measurement unit comprises a reagent pipette for aspirating a reagent in a reagent container held by the reagent container holder;
the reagent pipette comprises a liquid level sensor for detecting a liquid level of the reagent in the reagent container; and the operation of obtaining the remaining amount of the reagent in the first reagent container comprises operations of:
controlling the measurement unit to detect the liquid level of the reagent in the first reagent container by using the liquid level sensor when the measurement unit performs aspiration of the reagent in the first reagent container by using the reagent pipette; and
obtaining the remaining amount of the reagent in the first reagent container, based on a detection result by the liquid level sensor.

8. The sample analyzer of claim 6, wherein
the predetermined amount is a reagent amount necessary to perform single measurement for a predetermined measurement item.

9. The sample analyzer of claim 1, wherein
the operation of determining whether to switch from the first reagent container to the second reagent container comprises operations of:
obtaining information indicating an expiration date of the reagent in the first reagent container;
determining whether the expiration date of the reagent has expired; and
determining to switch from the first reagent container to the second reagent container when the expiration date of the reagent has expired.

10. The sample analyzer of claim 1, wherein
the measurement unit is configured to measure a measurement sample prepared from a blood sample and a reagent for blood coagulation measurement.

11. A sample analyzer comprising:
a reagent container holder configured to hold a first reagent container and a second reagent container, each of which contains a reagent of a same kind;
a measurement unit for aspirating a sample to be measured, and for measuring a measurement sample prepared from the sample and the reagent contained in the first reagent container or the second reagent container; and
an information processing unit configured to perform operations comprising:
receiving a start instruction to start successive measurement of a plurality of samples;
controlling the measurement unit to aspirate one sample and to measure a measurement sample prepared from the one sample and the reagent contained in the first reagent container according to the reception of the start instruction;
determining whether to switch from the first reagent container to the second reagent container after the aspiration of the one sample;
transmitting a start instruction to start quality control to the measurement unit and an aspiration stop instruction to stop sample aspiration when it is determined to switch from the first reagent container to the second reagent container;
controlling the measurement unit upon reception of the start instruction and the aspiration stop instruction to suspend a start of aspiration of a next sample, to aspirate a quality control sample, and to measure a quality control measurement sample prepared from the quality control sample and the reagent contained in the second reagent container;
determining whether an analysis result of the quality control measurement sample meets a predetermined condition; and
controlling the measurement unit to start the aspiration of the next sample and to measure a measurement sample prepared from the next sample and the reagent contained in the second reagent container, when the analysis result of the quality control measurement sample meets the predetermined condition, wherein both of the first reagent container and the second reagent container are held by the reagent container holder during suspension of the start of the aspiration of the next sample.

12. The sample analyzer of claim 11, wherein
the operation of determining whether to switch from the first reagent container to the second reagent container comprises operations of:
obtaining a remaining amount of the reagent in the first reagent container;
determining whether the remaining amount of the reagent in the first reagent container is less than a predetermined amount; and
determining to switch from the first reagent container to the second reagent container when the remaining amount of the reagent in the first reagent container is less than the predetermined amount.

13. The sample analyzer of claim 12, wherein
the measurement unit comprises a reagent pipette for aspirating a reagent in a reagent container held by the reagent container holder;
the reagent pipette comprises a liquid level sensor for detecting a liquid level of the reagent in the reagent container; and
the operation of obtaining the remaining amount of the reagent in the first reagent container comprises operations of:
controlling the measurement unit to detect the liquid level of the reagent in the first reagent container by using the liquid level sensor when the measurement unit performs aspiration of the reagent in the first reagent container by using the reagent pipette; and
obtaining the remaining amount of the reagent in the first reagent container, based on a detection result by the liquid level sensor.

14. The sample analyzer of claim 12, wherein
the predetermined amount is a reagent amount necessary to perform single measurement for a predetermined measurement item.

15. The sample analyzer of claim 11, wherein
the measurement unit is configured to measure a measurement sample prepared from a blood sample and a reagent for blood coagulation measurement.

16. A sample analyzing method comprising processes of:
(a) starting successive measurement of a plurality of samples by a measurement unit;
(b) determining whether to switch from a first reagent container to a second reagent container, each of which contains a same kind of reagent, while the measurement unit is performing the successive measurement by using the reagent contained in the first reagent container;
(c) transmitting a start instruction to start quality control and an aspiration stop instruction to stop sample aspiration to the measurement unit when it is determined to switch from the first reagent container to the second reagent container;
(d) upon reception of the start instruction and the aspiration stop instruction, suspending a start of aspiration of a next sample, aspirating a quality control sample, and measuring a quality control measurement sample prepared from the quality control sample and the reagent contained in the second reagent container by the measurement unit, when determined to switch from the first reagent container to the second reagent container; and
(e) starting the aspiration of the next sample by the measurement unit, when an analysis result of the quality control measurement sample meets a predetermined condition, wherein both of the first reagent container and the second reagent container are held by a reagent container holder during suspension of the start of the aspiration of the next sample.

17. The sample analyzing method of claim 16, wherein
the process (e) is performed when the analysis result of the quality control measurement sample is within a predetermined range.

18. The sample analyzing method of claim 16, further comprising a process of
(f) measuring a measurement sample prepared from the aspirated next sample and the reagent contained in the second reagent container by the measurement unit.

19. The sample analyzing method of claim 16, wherein the process (b) comprises operations of:
obtaining a remaining amount of the reagent in the first reagent container;
determining whether the remaining amount of the reagent in the first reagent container is less than a predetermined amount; and
determining to switch from the first reagent container to the second reagent container when the remaining amount of the reagent in the first reagent container is less than the predetermined amount.

20. A computer program product comprising:
a computer readable medium, and
software instructions, on the computer readable medium, for enabling a computer to perform predetermined operations comprising:
receiving a start instruction to start successive measurement of a plurality of samples;
controlling a measurement unit to start the successive measurement of the plurality of samples according to the reception of the start instruction;
determining whether to switch from a first reagent container to a second reagent container, each of which contains a same kind of reagent, while the measurement unit is performing the successive measurement by using the reagent contained in the first reagent container;
transmitting a start instruction to start quality control and an aspiration stop instruction to stop sample aspiration to the measurement unit when it is determined to switch from the first reagent container to the second reagent container;
controlling the measurement unit upon reception of the start instruction and the aspiration stop instruction to suspend a start of aspiration of a next sample, to aspirate a quality control sample, and to measure a quality control measurement sample prepared from the quality control sample and the reagent contained in the second reagent container, when determined to switch from the first reagent container to the second reagent container; and
controlling the measurement unit to start the aspiration of the next sample when an analysis result of the quality control measurement sample meets a predetermined condition, wherein both of the first reagent container and the second reagent container are held by a reagent container holder during suspension of the start of the aspiration of the next sample.

21. A sample analyzer comprising:

a reagent container holder configured to hold a first reagent container and a second reagent container, each of which contains a same kind of reagent;

a measurement unit configured to aspirate a sample to be measured, and to measure a measurement sample prepared from the sample and the reagent contained in the first reagent container or the second reagent container; and an information processing unit configured to perform operations comprising:

receiving a start instruction to start successive measurement of a plurality of samples;

controlling the measurement unit to start the successive measurement of the plurality of samples according to the reception of the start instruction;

when a remaining amount of the first reagent is less than a predetermined amount, controlling the measurement unit to suspend a start of aspiration of a next sample in the plurality of samples, to aspirate a quality control sample, and to measure a quality control measurement sample prepared from the quality control sample and the reagent contained in the second reagent container; and controlling the measurement unit to start the aspiration of the next sample in the plurality of samples when an analysis result of the quality control measurement sample meets a predetermined condition, wherein both of the first reagent container and the second reagent container are held by the reagent container holder during suspension of the start of aspiration of the next sample in the plurality of samples.

* * * * *